(12) United States Patent
Saint Victor

(10) Patent No.: US 8,778,860 B2
(45) Date of Patent: Jul. 15, 2014

(54) GREEN DISINFECTION/SANITIZATION COMPOSITIONS AND PROCESSES OF MAKING THEREOF

(75) Inventor: Marie-Esther Saint Victor, Glencoe, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 701 days.

(21) Appl. No.: 12/579,008

(22) Filed: Oct. 14, 2009

(65) Prior Publication Data

US 2010/0136148 A1  Jun. 3, 2010

(51) Int. Cl.
*C11D 3/16* (2006.01)
*C11D 3/22* (2006.01)
*C11D 17/04* (2006.01)

(52) U.S. Cl.
USPC ........... 510/101; 501/108; 501/181; 501/417; 501/463

(58) Field of Classification Search
USPC ................... 510/101, 108, 181, 417, 463
See application file for complete search history.

(56) References Cited

U.S. PATENT DOCUMENTS

| | | | |
|---|---|---|---|
| 4,915,955 A | 4/1990 | Gomori | |
| 5,356,479 A | 10/1994 | Menke et al. | |
| 5,403,587 A | 4/1995 | McCue et al. | |
| 5,531,938 A | 7/1996 | Erilli | |
| 5,591,708 A | 1/1997 | Richter | |
| 5,629,280 A | 5/1997 | Richter et al. | |
| 5,734,029 A * | 3/1998 | Wulff et al. ............ 536/4.1 | |
| 5,741,769 A | 4/1998 | Erilli | |
| 6,010,993 A | 1/2000 | Romano et al. | |
| 6,143,703 A | 11/2000 | Cheung et al. | |
| 6,184,190 B1 | 2/2001 | D'Ambrogio et al. | |
| 6,197,814 B1 | 3/2001 | Arata | |
| 6,346,281 B1 | 2/2002 | DeAth et al. | |
| 6,565,893 B1 | 5/2003 | Jones et al. | |
| 6,583,176 B2 | 6/2003 | Arata | |
| 6,767,876 B2 | 7/2004 | Khanuja et al. | |
| 6,846,498 B2 | 1/2005 | DeAth et al. | |
| 6,864,222 B1 | 3/2005 | Manske | |
| 6,951,833 B2 | 10/2005 | O'Neil | |
| 7,048,806 B2 | 5/2006 | Ochomogo et al. | |
| 7,261,905 B2 | 8/2007 | Arata et al. | |
| 7,351,684 B2 | 4/2008 | Tichy et al. | |
| 7,414,016 B1 | 8/2008 | van Buskirk et al. | |
| 7,432,234 B2 | 10/2008 | Ochomogo et al. | |
| 7,462,590 B2 * | 12/2008 | Tichy et al. ................... 510/372 |
| 7,465,697 B1 | 12/2008 | DeAth | |
| 7,470,331 B1 | 12/2008 | van Buskirk et al. | |
| 7,511,007 B2 | 3/2009 | Tichy et al. | |
| 7,608,573 B1 | 10/2009 | Scheuing et al. | |
| 7,618,931 B1 | 11/2009 | Scheuing et al. | |
| 2005/0274624 A1 | 12/2005 | Arata | |
| 2006/0034880 A1 | 2/2006 | Christmas et al. | |
| 2006/0040847 A1 | 2/2006 | Weibel | |
| 2006/0086048 A1 | 4/2006 | Romley | |
| 2006/0182813 A1 | 8/2006 | Holladay | |
| 2006/0216365 A1 | 9/2006 | Nassif et al. | |
| 2006/0293214 A1 | 12/2006 | Cheng et al. | |
| 2007/0259799 A1 | 11/2007 | Kubalik et al. | |
| 2007/0269530 A1 | 11/2007 | Arata et al. | |
| 2007/0281039 A1 | 12/2007 | DeAth | |
| 2008/0051312 A1 | 2/2008 | Lestage et al. | |
| 2009/0118154 A1 | 5/2009 | van Buskirk et al. | |
| 2001/0206790 * | 8/2011 | Wiess ............................ 424/725 |

FOREIGN PATENT DOCUMENTS

| | | |
|---|---|---|
| DE | 199 18 189 A1 | 10/2000 |
| EP | 1278420 | 12/2005 |
| EP | 1948769 | 3/2009 |
| JP | 2006182662 * | 7/2006 |
| WO | 96/28033 A1 | 9/1996 |
| WO | WO01/84936 | 11/2001 |
| WO | 2006/071069 A1 | 7/2006 |
| WO | WO2008/015381 | 2/2008 |
| WO | WO2008/052303 | 5/2008 |
| WO | WO2009/037231 | 3/2009 |

OTHER PUBLICATIONS

IndiaDivine; Colloidal silver tooth soap and oil of oregano; Online, URL< http://www.indiadivine.org/audarya/ayurveda-health-wellbeing/996484-colloidal-silver-tooth-soap-oil-oregano.html> Jun. 13, 2008 (accessed Dec. 17, 2011), 3 pages.*
PCT/US2010/002749 International Search Report dated Jan. 20, 2011.

* cited by examiner

Primary Examiner — Patricia Leith

(57) ABSTRACT

Cleaning and disinfecting compositions containing one or more "green" surfactants are disclosed. The compositions may be present as micro-emulsions that generally include green disinfecting agents, green surfactants, and water. The composition may also contain other green ingredients such as linkers, pH adjusting agents, natural fragrances, natural insecticides, and other natural organic actives such as natural oils. The composition may be used as a green cleaning and disinfecting composition with performance comparable or superior to conventional cleaning and disinfecting products with less desirable ecological profiles.

6 Claims, No Drawings

GREEN DISINFECTION/SANITIZATION COMPOSITIONS AND PROCESSES OF MAKING THEREOF

BACKGROUND

1. Technical Field

Eco-friendly, or "green," disinfection/sanitization compositions are disclosed that include "green" disinfecting/sanitizing agents, "green" surfactants, and other "green" ingredients such as linkers, pH adjusting agents, natural fragrances, and other "green" additives. The composition may be used as a "green" cleaning and disinfecting/sanitizing composition with performance comparable or superior to conventional products with less desirable ecological profiles. The composition may be present as a micro-emulsion.

2. Description of the Related Art

In recent years, there has been a significant amount of global consumer awareness in "green", i.e., eco-friendly, household or personal care products. As a result, increasing efforts have been directed to the development of household products with desirable ecological profiles. For example, products containing ingredients that are derived from natural and renewable sources, as well as products that are biodegradable in natural environments, have been a focus of this global "eco-friendly" trend.

Indeed, products derived from renewable resources, such as plants, contribute less greenhouse gas because of their closed $CO_2$ cycle. Specifically, during growth, plants consume the same amount of carbon dioxide ($CO_2$) and water ($H_2O$) as they subsequently release into the atmosphere by biodegradation after use. Therefore, products derived from renewable resources, such as plants, are considered to be "green" and having zero or reduced "carbon footprint" when compared with petrochemical-based products. Common ingredients in household products such as surfactants, fragrances, oils and solvents can be derived directly or indirectly from both renewable sources such as plant materials or non-renewable sources such as petroleum.

Further, multi-purpose household products that function both as cleaners and disinfectants/sanitizers are also known in the art. However, cleaners with good cleaning performance sometimes have poor disinfecting/sanitizing properties, while disinfectants/sanitizers that demonstrate excellent disinfecting/sanitizing performance sometimes have poor cleaning properties. Moreover, products that combine good cleaning and disinfecting/sanitizing efficiencies typically include harsh chemicals, such as peroxygen bleach, hydrogen peroxide, glutaraldehyde and quaternary ammonium salts, which not only are toxic and/or incompatible to human skin but also have a less desirable ecological profile by including non-natural ingredients.

Natural and non-toxic disinfecting/sanitizing agents are known in the art. For example, naturally occurring essential oils and colloidal silver are both effective disinfecting/sanitizing agents with good antimicrobial activity. However, because essential oils and colloidal silver are generally immiscible with water, compositions based thereon typically include surfactants and/or solvents to disperse or solubilize the essential oils or colloidal silver. Nevertheless, the surfactants used in the compositions generally include petroleum-based surfactants which may lead to the formation of a less stable and less eco-friendly disinfectant composition.

While most surfactants are still derived from petroleum chemicals, surfactants derived from plant-based carbohydrates and oils are becoming available. One suitable renewable raw material for surfactant production is glucose, which is reacted with alcohol to produce alkyl polyglycosides (also known as alkyl polyglucosides). Alkyl polyglycosides have been used in cosmetics products, agricultural formulations and as surfactants in industrial cleaning agents. Alkyl polyglycosides include a hydrophobic (or lipophilic) hydrocarbon chain is formed by a fatty alcohol (e.g., dodecanol, tetradecanol) obtained from a saturated tropical oils such as palm or coconut oil. The hydrophilic part of an alkyl polyglycoside molecule is derived from glucose or dextrose and may be obtained from starch, most commonly from corn.

Another group of surfactants derived from natural and renewable sources are amino acid-based surfactants, which are based on fatty acids and natural amino acids. In addition to their desirable ecological profile, both alkyl polyglycosides and amino acid-based surfactants have good compatibility with the eyes, skin and mucous membranes and even reduce the irritant effects of surfactant combinations. Both alkyl polyglycosides and amino acid-based surfactants are completely biodegradable, both aerobically and anaerobically.

Some anionic surfactants may also have immediate precursors that are obtainable from natural and renewable sources. For example, long-chain alkyl sulfates may be conveniently prepared from fatty alcohols derived from coconut oils. In particular, sodium coco sulfate (SCS) is derived from pure coconut oil and includes a mixture of sodium alkyl sulfate with the main component being sodium lauryl sulfate. Sodium coco sulfate may be used in a wide variety of consumer products in which viscosity building and foam characteristics are of importance. It can be incorporated into shampoos, hand soaps, bath products, shaving creams and medicated ointments.

Finally, conventional cleaning and disinfecting/sanitizing compositions are generally formulated by mixing surfactants, disinfectants, water and other ingredients to form a relatively uniform composition. The process typically requires application of mechanical force (i.e. stirring) and/or heat, both of which consume energy and resources. As a result, the ecological profile of the compositions thus formed may be adversely affected.

Hence, there is a need for a cleaning and disinfecting/sanitizing composition derived from natural, renewable sources or having a higher percentage of components that are derived from natural, renewable sources. Moreover, there is a need for a green cleaning and disinfecting/sanitizing composition with an improved ecological profile and performance that is comparable, or even superior, to conventional cleaning and disinfecting/sanitizing products with less desirable ecological profiles. Finally, there is a need for a process for manufacturing green composition that does not require consumption of additional mechanical or heat energies.

SUMMARY OF THE DISCLOSURE

In satisfaction of the aforementioned needs, cleaning and disinfecting/sanitizing compositions containing one or more green surfactants are disclosed. The compositions may be present as micro-emulsions that generally include green disinfecting/sanitizing agents, green surfactants, and water. The composition may also contain other green ingredients such as linkers, pH adjusting agents, natural fragrances, natural insecticides, and other natural organic actives such as natural oils. The composition may be used as a green cleaning and disinfecting/sanitizing composition with performance comparable or superior to conventional products with less desirable ecological profiles.

As used in this disclosure, a "green" ingredient is defined as a substance that is obtainable from natural and renewable sources or is prepared from immediate precursor(s) obtainable from natural and renewable sources.

As used herein, the term "Natural Index" (NI) is the weight percentage of the composition that includes ingredients that are either directly obtainable from natural and renewable sources or made from immediate predecessors that are directly obtainable from natural and renewable sources.

For example, ingredients such as water, ethanol, lactic acid, citric acid, caustic soda, natural fragrances, are both green and contribute to the NI of a disclosed composition because each is obtainable from natural and renewable sources. Similarly, compounds like alkyl polyglycosides, alkyl glucoside, sodium coco sulfate (sodium lauryl sulfate) as disclosed herein are both green and contribute to the NI of a disclosed composition because each may be made from immediate precursors (fatty alcohols, glucose, etc.) that are obtainable from natural and renewable sources. On the other hand, surfactants such as ethoxylated nonionic surfactants, alkylbenzene sulfonate anionic surfactants, and quaternary ammonium cationic surfactant are based on petroleum chemicals and thus are not green as defined herein and do not contribute toward the NI of the composition.

In a general embodiment, the disclosed cleaning and disinfecting/sanitizing composition may include at least one green surfactant, at least one essential oil as a natural disinfecting/sanitizing agent, and water. In a refinement, the green surfactant may include a nonionic surfactant such as an alkyl polyglycoside, an anionic surfactant such as sodium lauryl sulfate or sodium coco sulfate, or a mixture of both. The essential oil may be any known plant extract that exhibit effective antimicrobial activities. The combination of green surfactant and essential oil may synergistically improve disinfecting/sanitizing performance of the composition.

The disclosed composition may further optionally include an additional green disinfecting/sanitizing agent to further improve the disinfecting performance of the composition. In one embodiment, the additional green disinfecting/sanitizing agent may be colloidal silver suspended in a micro-emulsion formed by the rest of the ingredients of the composition. It is contemplated that the micro-emulsion containing green surfactant(s) and essential oil(s) may not only stabilize the colloidal silver but also synergistically combine with colloidal silver to further improve the disinfecting/sanitizing performance of the composition.

In a further embodiment, the disclosed composition may be made by forming a mixture that includes at least one green surfactant, at least one essential oil, and water, and allowing the mixture to simultaneously form a micro-emulsion without heating. The formation of the mixture may be achieved without mechanical agitation, such as through a stirring machine, a shaker, or other mechanical equipment that consumes electricity. In a refinement, the method of forming the disclosed composition may further include the optional step of suspending colloidal silver in the micro-emulsion. Because the disclosed method does not require additional electric or heat energy that may be necessary in the formulation of conventional cleaning and disinfecting/sanitizing compositions, the ecological profile of the disclosed composition may be further improved.

The disclosed composition may further include additional green ingredients such as green linkers, green pH adjusting agents, natural fragrances, etc. In particular, the inclusion of one or more green linkers in the composition may further facilitate the formation of a micro-emulsion. Moreover, the green pH adjusting agents may include one or more organic acids that also function to remove soap scum and lime scale from a target surface.

The green surfactant(s) and other green ingredients of the disclosed composition may not only improve the ecological profile of the compositions but also allow spontaneous formation of a stable micro-emulsion at room temperature. It is contemplated that the presence of the disclosed composition as a micro-emulsions, rather than solutions or conventional emulsions, may contribute to the enhanced performance of the composition by, among other things, stabilizing the green disinfecting/sanitizing agents included therein.

Finally, disinfecting performance of the disclosed composition is evaluated through various comparison tests between the disclosed composition and one or more leading commercial products with less desirable ecological profiles, i.e. with lower Natural Index than the disclosed composition. As discussed in greater detail below, the performance of the disclosed composition is at least comparable to, and in some cases better than, the leading commercial products.

Other advantages and features of the disclosed methods and compositions will be described in greater detail below. It will also be noted here and elsewhere that the disclosed green compositions may be suitably modified to be used in a wide variety of household applications by one of ordinary skill in the art without undue experimentation.

DETAILED DESCRIPTION OF THE PRESENTLY PREFERRED EMBODIMENTS

This disclosure is generally related to an eco-friendly liquid compositions or emulsions. To evaluate the ecological profile a composition or emulsion, the term Natural Index (NI) is used herein to refer to the weight percentage of the composition that includes ingredients that are either directly obtainable from natural and renewable sources or made from immediate predecessors that are directly obtainable from natural and renewable sources. Similarly, a green ingredient is defined as a substance that is obtainable from natural and renewable sources or is prepared from immediate precursor (s) obtainable from natural and renewable sources. For example, ingredients such as water, ethanol, lactic acid, citric acid, caustic soda, natural fragrances, are all obtainable from natural and renewable sources while synthetic fragrances are not. Similarly, compounds like alkyl polyglycosides, alkyl glucoside, sodium coco sulfate (sodium lauryl sulfate) disclosed herein may be made from immediate precursors (fatty alcohols, glucose, etc.) that are obtainable from natural and renewable sources. On the other hand, surfactants such as ethoxylated nonionic surfactants, alkylbenzene sulfonate anionic surfactants, and quaternary ammonium cationic surfactant are based on petroleum chemicals, are therefore not green and do not contribute toward the NI of a composition.

In a general embodiment, the disclosed green composition is aqueous-based and may include at least one green surfactant that is made from immediate precursors that are obtainable from natural and renewable sources. The composition may also include at least one green disinfecting/sanitizing agent, such as essential oil and colloidal silver, to provide disinfecting/sanitizing benefit to a target surface. The composition may further include additional green ingredients such as natural fragrances, green linkers, green pH adjusting agents, etc. In some embodiments, the disclosed composition may also include an organic solvent, while in other embodiments the composition is essentially free of organic solvents.

Green Surfactants

The green nonionic surfactants of the disclosed composition may include, but are not limited to, sugar-based surfactants, polyol-based surfactants, alkyl ethers, and alkyl carbonates. The sugar-based surfactants may be alkyl polyglycoside (or alkyl polyglucoside) surfactants that are made from fatty alcohols in coconut oil and polyglucose in corn. In addition to its excellent ecological profile, alkyl polyglycosides are biodegradable, non-irritating to human skin, and effective in solubilizing fragrance oil in water.

The alkyl polyglycosides which can be used in the disclosed emotions correspond to the following Formula I:

$$R_1O(Z)_a \quad (I)$$

wherein $R_1$ is a monovalent organic radical having from about 4 to about 22 carbon atoms; Z is a saccharide residue having 5 or 6 carbon atoms; and a is a number having a value from 1 to about 6. For example, alkyl polyglycosides of formula I wherein Z is a glucose residue may be utilized. Such alkyl polyglycosides are commercially available, for example, as APG®, GLUCOPON®, or PLANTAREN® surfactants from Cognis, 5051 Estecreek Drive, Cincinnati, Ohio 45232.

Suitable alkyl ethers used as green surfactants in the disclosed composition may include ethers with $C_4$-$C_{22}$ alkyl chains on either side of the C—O—C bond ($R_1$—O—$R_2$). The alkyl chains ($R_1$, $R_2$) may be saturated or unsaturated. In one embodiment, the alkyl ether may be dicaprylyl ether and included in the disclosed composition as a mixture with decyl glucoside and glyceryl oleate available under Plantasil® Micro from Cognis, 5051 Estecreek Drive, Cincinnati, Ohio 45232.

Suitable alkyl carbonates used as green surfactants in the disclosed composition may include carbonates with $C_4$-$C_{22}$ alkyl chains on either side of the carbonate group

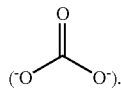

The alkyl chains may be saturated or unsaturated. In one embodiment, the alkyl ester may be dicaprylyl carbonate.

Other nonionic green surfactants suitable for use in the disclosed composition may include, but are not limited to, alkyl glucose amide, triglycerides, N-methyl coconut fatty acid glucamides (C12-14), amino acid-based surfactants, sugar esters, sorbital esters, sterol esters, glycolipid biosurfactants, etc.

In one embodiment, the disclosed composition may include from 0.25 to 3.0 wt % green nonionic surfactant(s). In another embodiment, the green nonionic surfactant(s) may be included at a level of from 0.25 to 1.5 wt %.

In addition to the green nonionic surfactant, the disclosed composition may optionally include one or more green anionic surfactants. The green anionic surfactants may also be prepared from immediate precursors that are obtainable from natural and renewable sources. In one embodiment, the green anionic surfactants include one or more long-chain alkyl sulfates. Suitable alkyl sulfates includes, but are not limited to, sodium $C_8$-$C_{20}$ sulfates, ammonium $C_8$-$C_{20}$ sulfates, and mixtures thereof.

In a preferred embodiment, the green anionic surfactant includes sodium coco sulfate or sodium lauryl sulfate. Sodium coco sulfate may be prepared from sulfating coconut oil, which is made up of a wide range of fatty acids (ranging from as few as 8 carbon alkyl chains to as many as 20). The majority, e.g. 45-50%, of the fatty acids in coconut oil are fatty acids containing 12 carbons. Sodium lauryl sulfate, on the other hand, is a purified version of the sodium coco sulfate. During manufacturing of sodium lauryl sulfate, coconut oil is processed to remove most of the non-12 carbon fatty acids before the fatty acids are sulfated.

The green anionic surfactant may be used in the disclosed composition to synergistically improve the performance, such as soil removal, of the composition. Accordingly, a relatively low level of the green anionic surfactant is required. For example, the concentration of the green anionic surfactant(s) may be from 0 to 3.0 wt %, from 0.0001 to 2.5 wt % or even from 0.001 to 2 wt %.

Another group of green surfactants suitable for use in the disclosed composition are amino acid-based surfactants, which are biomimetic surfactants derived from fatty acids (from vegetable oils) and naturally produced amino acids. The amino acid-based surfactants may be anionic, cationic, or nonionic. Further, the amino acid-based surfactants may be not only highly surface active but also active against microbes, bacteria, and fungi.

The amino acid used in the surfactants may include, but are not limited to aspartic acid, glutamic acid, arginine, alanine, glycine, sarcosine, leusine, proline, serine, etc. The amino acids moiety may be coupled to the fatty acids moiety through N-acyl, N-aryl, or O-alkyl ester linkages. Moreover, depending on the structure of the fatty acids used, the amino acid-based surfactants may be linear with a single chain, dimeric or glycerized.

Exemplary amino acid-based surfactants include N-acyl sarcosinate and N-acyl glutamate surfactants (Perlastan® from Schill & Seilacher or Struktol); surfactants derived from L-arginine and coconut fatty acid (AminoSoap® from Ajinomoto), surfactants derived from L-glutamic acid and phytosterol (Eldew® from Ajinomoto); and surfactants derived from glycine and coconut fatty acid (Amilite® from Ajinomoto).

Of course, the type, strength, and concentration of the essential oils suitable for use in the disclosed composition would be apparent to one of ordinary skill in the art and therefore should not be considered as limiting the scope of this disclosure.

Green Disinfecting/Sanitizing Agents

As discussed above, the disclosed composition includes at least one green disinfecting/sanitizing agent for providing antimicrobial benefit to a target surface. The green disinfecting/sanitizing agent may be one or more essential oil, colloidal silver, and a mixture of both.

Under the EPA guidelines (http://www.epa.gov/oppad001/ad_info.htm), disinfectants are used on hard inanimate surfaces and objects to destroy or irreversibly inactivate infectious fungi and bacteria but not necessarily their spores; and sanitizers are used to reduce, but not necessarily eliminate, microorganisms from the inanimate environment to levels considered safe as determined by public health codes or regulations. In one embodiment, the disclosed composition may be used as a disinfectant. In another embodiment, the disclosed composition may be used as a sanitizer.

Essential oils for the disclosed composition may include plant extracts that exhibit antimicrobial, antibacterial and/or antifungal activities. For example, suitable essential oils may include, but are not limited to, citronella oil, lemon eucalyptus oil, cinnamon oil, castor oil, rosemary oil, lemongrass oil, cedar oil, peppermint oil, clove oil, geranium oil, verbena oil, pennyroyal oil, lavender oil, pine oil, cajeput oil, basil oil, thyme oil, allspice oil, soybean oil, garlic oil, etc.

In one embodiment, the essential oil is selected from the group consisting of oregano oil, thyme oil, clove oil, rosemary oil, garlic oil, cinnamon oil, bay oil, lemongrass oil, Australian tea tree oil, citronella oil, geranium oil, avocado oil, and mixtures thereof. The essential oils may be included in the composition at a concentration of 0.001-2 wt %, more preferably at a concentration of 0.01-1 wt %. Of course, the type, strength, and concentration of the essential oils suitable for use in the disclosed composition would be apparent to one of ordinary skill in the art and therefore should not be considered as limiting the scope of this disclosure.

As another suitable green disinfecting/sanitizing agent, silver exhibits broad spectrum of activity and has been registered as a disinfectant with the EPA for over fifty years. In particular, colloidal silver is safe and effective in lower concentrations and is suitable for use in the disclosed composition. Colloidal silver may be electrolytically produced with a particle size of 0.001 to 0.01 micron. In one embodiment, the charged silver particles in the colloidal silver are complexed with citric acid, although other acids, such as acetic acid, may also be used to from the silver complex. To further improve the disinfecting/sanitizing performance of the composition, the colloidal silver may be stabilized and/or suspended, such as in a micro-emulsion, to prevent aggregation (or "falling out") of the silver particles.

In one embodiment, the colloidal silver used in the disclosed composition is available under Tinosan® SDC by Ciba Corporation, 4090 Premier Dr., High Point, N.C. 27265. The colloidal silver may be included in the composition at a concentration of 20-2000 ppm, more preferably at a concentration of 30-1000 ppm. However, it is to be understood that the type, strength, and concentration of the colloidal silver suitable for use in the disclosed composition would be apparent to one of ordinary skill in the art and therefore should not be considered as limiting the scope of this disclosure.

Green Linkers

The disclosed composition may optionally include one or more green linkers. The green linkers may be lipophilic or hydrophilic. Suitable lipophilic and hydrophilic linkers may include, but are not limited to, oleates (e.g., glycerol monooleate (GMO), glyceryl oleate, etc.), stearates (e.g., glycerol monostearate (GMS)), polysorbates (e.g., sorbitan monolaurate (SML)), fatty alcohols, glucosides, esters, glycerin and mixtures thereof.

For example, the lipophilic linker may include one or more C12-18 fatty alcohols. In one embodiment, the one or more fatty alcohols may be selected from the group consisting of lauryl alcohol, cetyl alcohol, myristic alcohol, and mixtures thereof. The alkanols may be made from immediate predecessors that are obtainable from natural and renewable sources. In particular, lauryl alcohol may be made from fatty acids in coconut oils; cetyl alcohol may be made from spermaceti, a waxy substance obtained from sperm whale oil; and myristic alcohol may be made from myristic acid, which is found in palm oil, coconut oil, butter fat, and spermaceti.

Similarly, the hydrophilic linker may also be made from immediate predecessors that are obtainable from natural and renewable sources. Suitable hydrophilic linkers may include one or more alkyl glucoside such as hexyl glucoside. The hexyl glucoside used in the disclosed composition is commercially available (as "AG 6206") from Akzo Nobel, 525 W. Van Buren Street, Chicago, Ill. 60607-3823. The hydrophilic part of the hexyl glucoside, derived from glucose or dextrose, may be obtained from starch, most commonly from corn.

Without wishing to be bound by any particular theory, linker molecules are added to the disclosed composition to enhance the interaction between the surfactant and oil (lipophilic linkers) or water (hydrophilic linkers) phases, where the lipophilic and hydrophilic linkers are combined to behave as a self-assembled surfactant at the oil/water interface to facilitate the formation of a stable micro-emulsion. Further, the efficiency of the self-assembly may be dependent on the ratio of the green surfactants and the green linkers, the total concentration of the surfactants and/or linkers, or both. Moreover, the green lipophilic and/or hydrophilic linkers may be used in the disclosed composition not only to synergistically improve the cleaning performance of the composition but also promote the spontaneous formation of a micro-emulsion without consumption of heating or electric energy.

In some embodiments, the self-assembly between hydrophilic and lipophilic linkers to facilitate the formation of micro-emulsions may require the presence of only a small amount of linkers, such as no more than 0.1 wt %, 0.05 wt %, or even 0.01 wt %. In one embodiment, effective soil removal and/or spontaneous formation of a micro-emulsion can be achieved by a composition using linkers at a total concentration of 0.0001-0.01 wt %. It is to be understood that the green linkers may be used in other form of the disclosed composition as well, such as in a solution or a conventional emulsion.

Natural (Green) Fragrances

The disclosed composition may include one or more fragrances derived in from natural and renewable sources such as plants or crops. In addition, the composition may deliver the natural fragrances into the air in a controlled manner over a long period of time. To that end, the presence of the composition as micro- or nano-emulsions may facilitate the consistent release of the fragrances.

For example, the disclosed composition may include a natural fragrance for air freshening. The natural fragrance freshens air either by masking one or more malodors therein or by imparting a pleasant smell to the air, or both. As is well known, a fragrance normally consists of a mixture of a number of fragrant materials, each of which has a particular fragrance. The number of fragrant materials in a fragrance is typically ten or more. The range of fragrant materials used may vary. The materials come from a variety of chemical classes, but in general are water-insoluble oils. In many instances, the molecular weight of a fragrance material is in excess of 150, but does not exceed 300.

The natural fragrance included in the disclosed composition may be present in an amount that is sufficient to impart a pleasant smell to the air that can be perceived by a consumer. In the presence of a malodor, the natural fragrance may be present in an amount that masks at least a substantial portion of the malodor in the air. More preferably, the natural fragrance included in the disclosed composition may be present in an amount that not only completely masks the malodors therein, but also delivers a pleasant smell to be perceived by a consumer.

The natural fragrance may be present in the disclosed composition in an amount of from 0 to 1.5 wt %, from 0 to 0.15 wt %, or sometime from 0 to 0.015 wt %. The amount of the fragrance that is needed to mask the malodor(s) therein, and/or the amount of the fragrance to impart the pleasant smell to be perceived by the consumer will be apparent to one of ordinary skill in the art.

The fragrance according to this disclosure may comprise one or more fragrant materials or materials that provide chemically active vapors. In one embodiment, the fragrance can comprise and/or include volatile, fragrant compounds including, but not limited to natural botanic extracts, essences, fragrance oils, and so forth. As is known in the art, many essential oils and other natural plant derivatives contain large percentages of highly volatile scents. In this regard, numerous essential oils, essences, and scented concentrates are commonly available from companies in the fragrance and food businesses.

Exemplary oils and extracts include, but are not limited to, those derived from the following plants: almond, amyris, anise, armoise, bergamot, cabreuva, *calendula*, canaga, cedar, chamomile, coconut, eucalyptus, fennel, jasmine, juniper, lavender, lemon, orange, palm, peppermint, quassia, rosemary, thyme, and so forth.

Fragrances can also be made of organic compounds derived from floral materials and fruits. Examples of suitable organic compounds include, but are not limited to, dimyrcetol, phenylethyl alcohol and tetrahydromuguol, decyl aldehyde, undecyl aldehyde, undecylenic aldehyde, lauric aldehyde, amyl cinnamic aldehyde, ethylmethyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, parahydroxyphenolbutanone, 6-acetyl-1,1,3,4,4,6-hexamethyl tetrahydronaphthalene, alpha-methyl ionone, gamma-methyl ion-one, and amyl-cyclohexanone and mixtures thereof.

It is to be understood, of course, that the type, strength, and odor profile of the fragrance suitable for use in the disclosed aerosol composition would be apparent to one of ordinary skill in the art and therefore should not be considered as limiting the scope of this disclosure.

Green pH Adjusting Agents

In some embodiment, the disclosed composition may optionally include one or more pH adjusting agents. Preferably, the pH adjusting agents used in the composition are derived from natural and renewable sources and thus do not negatively affect the ecological profile, i.e. Natural Index, of the composition.

Suitable pH adjusting agents may include bases such as sodium hydroxide (manufactured through electrolysis of salt solution), sodium carbonate (naturally occurring as mineral deposits), and sodium bicarbonate (naturally occurring in mineral natron). In addition, the green pH adjusting agents may include one or more organic acids derived from natural or renewable sources. For example, the organic acids may be citric acid (naturally occurring in fruits and vegetables), lactic acid (obtainable from fermentation of milk sugar, cornstarch, or potato), acetic acid (obtainable from fermentation of starch or fruit), etc. The use of lactic or citric acids may also have the benefit of soap scum and lime scale removal, as well as anti-streaking. Finally, the green pH adjusting agents may include one or more salts of the aforementioned organic acids, such as sodium citrate, sodium acetate, etc.

In one embodiment, the disclosed composition includes 1.0-3.0 wt % lactic acid. In another embodiment, the composition includes a mixture of lactic acid and tartaric acid. It is to be understood, of course, that the type and concentration of the green pH adjusting agents suitable for use in the disclosed composition would be dependent on the desired pH of the composition and should be apparent to one of ordinary skill in the art without undue experimentation in light of this disclosure.

One feature of the disclose composition is its physical presence as a micro-emulsion in some embodiments. Without being wishing to be bound by any particular theory, it is contemplated that micro-emulsions of the disclosed green ingredients exhibit improved performance in both cleaning and disinfecting/sanitizing than conventional emulsions, suspensions, or even solutions. However, it is to be understood that the disclosed composition may also be present as a solution, conventional emulsion, or even suspension in other embodiments.

Another feature of the disclosed composition is its high Natural Index. As a result, the composition achieves improved performance without sacrificing the ecological profile thereof. For example, the composition may have a high Natural Index of no less than 95%, 97%, 98%, or even 98.5%. In one embodiment, the disclosed composition has a Natural Index of no less than 99%, 99.5% or 99.8%.

Non-limiting examples of the disclosed compositions according to this disclosure are listed below:

Composition I

| Function/Description | Chemical Name/Trade Name | Concentration |
| --- | --- | --- |
| Surfactant | Alkylpolyglycoside | 0.25-1.5% |
| Disinfectant | Colloidal silver | 300-1000 ppm |
| Fragrance | Fragrance | 0-0.015% |
| Solvent | Water | Balance |

Composition II

| Function/Description | Chemical Name/Trade Name | Concentration |
| --- | --- | --- |
| Surfactant | Alkylpolyglycoside | 0.25-1.5% |
| Lipophilic linker | Fatty Alcohol | 0-0.01% |
| Hydrophilic linker | Alkyl glucoside | 0-0.01% |
| Disinfectant | Colloidal silver | 300-1000 ppm |
| Fragrance | Fragrance | 0-0.015% |
| Solvent | Water | Balance |

Composition III

| Function/Description | Chemical Name/Trade Name | Concentration |
| --- | --- | --- |
| Surfactant | Alkylpolyglycoside | 0.25-3.0% |
| Surfactant | Sodium coco sulfate | 0-3.0% |
| Disinfectant | Thyme and oregano oils | 0.01-1.0% |
| Fragrance | Fragrance | 0-0.15% |
| Solvent | Water | Balance |

Composition IV

| Function/Description | Chemical Name/Trade Name | Concentration |
| --- | --- | --- |
| Surfactant | Alkylpolyglycoside | 0.25-3.0% |
| Surfactant | Sodium coco sulfate | 0-3.0% |
| Disinfectant | Colloidal silver | 300-1000 ppm |
| Fragrance | Fragrance | 0-0.15% |
| Solvent | Water | Balance |

Composition V

| Function/Description | Chemical Name/Trade Name | Concentration |
| --- | --- | --- |
| Surfactant | Dicaprylyl ether, hexyl glucoside, and glyceryl oleate/Plantasil ® Micro | 0.1-3.0% |
| Surfactant | Alkylpolyglycoside | 0.25-3.0% |
| Surfactant | Sodium coco sulfate | 0-3.0% |
| Disinfectant | Thyme and oregano oils | 0.01-1.0% |
| Fragrance | Fragrance | 0-0.15% |
| Solvent | Water | Balance |

Composition VI

| Function/Description | Chemical Name/Trade Name | Concentration |
|---|---|---|
| Surfactant | Dicaprylyl ether, hexyl glucoside, and glyceryl oleate/ Plantasil ® Micro | 0.1-3.0% |
| Surfactant | Sodium coco sulfate | 0.1-2.5% |
| Organic acid | Lactic acid | 1.0-3.0% |
| Disinfectant | Colloidal silver | 300-1000 ppm |
| Fragrance | Fragrance | 0-1.5% |
| Solvent | Water | Balance |

To make the disclosed compositions as micro-emulsions, the ingredients, such as the green surfactant, the green disinfecting/sanitizing agent, water, and other green additives may be mixed together to allow simultaneous formation of a micro-emulsion without heating. In some embodiments, the formation of the mixture may be achieved without any electromechanical agitation, such as through a stirring machine, a shaker, or other mechanical equipment that consumes electricity. Rather, the mixing of the ingredients may be simply achieved through manual swirling, stirring, or shaking. Because the disclosed method does not consume additional electric or heat energy that may be necessary in the formulation of conventional cleaning and disinfecting/sanitizing compositions, the ecological profile of the disclosed composition may be further improved.

In order to evaluate the disinfecting performance of the disclosed composition, the above-listed exemplary compositions I-VI are tested against Staphylococcus aureus, obtained from the American Type Culture Collection, Manassas, Va. Transfers are used within 7 days of stock culture. The performance tests use the following standard AOAC Germicidal Spray Test.

Test Method

A 48 hour culture of the aforementioned bacteria with 5% fetal bovine serum is dried onto a number of clean, sterile glass test surfaces (test tubes). The dry, contaminated test surfaces are then sprayed, individually, with the test compositions. In the initial and follow-up tests, respectively, 30 and 60 contaminated test surfaces were treated with the test compositions. Contaminated test surfaces are then allowed to incubate in the disinfectant for 10 minutes contact time at room temperature (23° C.).

After the contact time has elapsed, the treated test surfaces are transferred, individually at intervals, to sterile test tubes or jars containing a liquid growth medium that has been amended with chemical agents to immediately neutralize the action of the test composition.

The treated test surfaces are then incubated in the neutralizing growth medium for 48 hours. After incubation, the number of tubes showing growth of the target microorganism is recorded. To "pass" an initial 30 carrier test, at least 29 of the 30 surfaces tested must demonstrate complete disinfection (no detectable growth of the target microorganism in the test tubes containing neutralizing growth medium). To "pass" a follow-up 60 carrier test, at least 59 of the 60 surfaces tested must demonstrate complete disinfection.

The results reported as n+/N where n indicates the number of failures or tubes positive for growth in N replicates (N=30 or 60). In order to pass the standard disinfectant evaluation, a product can have no more than 1 failure in 30 or 60 replicates (passing results: 0+/30, 1+/30, 0+/60, or 1+/60; anything greater indicates a failing result).

The test results for each exemplary composition is listed below:

| Composition | Initial Test Result | Follow-up Test Result |
|---|---|---|
| I | 0+/30 | 0+/60 |
| II | 0+/30 | 0+/60 |
| III | 0+/30 | 0+/60 |
| IV | 0+/30 | 0+/60 |
| V | 0+/30 | 0+/60 |
| VI | 0+/30 | 0+/60 |

The results of this screening demonstrate that the disclosed compositions are capable of achieving disinfectant efficacy against Staphylococcus aureus within a 10-minute contact time. On the other hand, the control samples (untreated with any disinfectant composition) all tested positive for growth of the target microorganism ($>1.0\times10^4$ CFU/carrier).

While only certain embodiments have been set forth, alternatives and modifications will be apparent from the above description to those skilled in the art. These and other alternatives are considered equivalents and within the spirit and scope of this disclosure and the appended claims.

What is claimed is:

1. A cleaning composition comprising:
   from 0.1 to 3.0 wt % of a mixture of surfactants including dicaprylyl ether, hexyl glucoside and glyceryl oleate;
   from 0.25 to 3.0 wt % alkylpolyglycoside;
   from 0.1 to 3.0 wt % sodium coco sulfate;
   at least one essential oil; and
   water.

2. The composition of claim 1, wherein the at least one essential oil is selected from the group consisting of oregano oil, thyme oil, clove oil, rosemary oil, garlic oil, cinnamon oil, bay oil, lemongrass oil, Australian tea tree oil, citronella oil, geranium oil, avocado oil, and mixtures thereof.

3. A cleaning composition comprising:
   from 0.1 to 3.0 wt % of a mixture of surfactants including dicaprylyl ether, hexyl glucoside and glyceryl oleate;
   from 1.0 to 3.0 wt % lactic acid;
   from 0.1 to 3.0 wt % sodium coco sulfate;
   at least one essential oil;
   from 300 to 1000 ppm colloidal silver; and
   water.

4. The composition of claim 3, further comprising alkylpolyglycosides.

5. The composition of claim 3, wherein the at least one essential oil is selected from the group consisting of oregano oil, thyme oil, clove oil, rosemary oil, garlic oil, cinnamon oil, bay oil, lemongrass oil, Australian tea tree oil, citronella oil, geranium oil, avocado oil, and mixtures thereof.

6. A method for disinfecting or sanitizing a surface, comprising administering to the surface, the cleaning composition of claim 1, claim 2, claim 3 or claim 5.

* * * * *